(12) United States Patent
Hanks et al.

(10) Patent No.: US 12,006,495 B2
(45) Date of Patent: Jun. 11, 2024

(54) SOLAR STEAM EXPLOSION OF ALGAE

(71) Applicant: ExxonMobil Technology and Engineering Company, Annandale, NJ (US)

(72) Inventors: Patrick L. Hanks, Bridgewater, NJ (US); Everett J. O'Neal, Asbury, NJ (US); Sarah E. Feicht, Raritan, NJ (US); Mark A. Deimund, Jersey City, NJ (US); Vinit Choudhary, Cypress, TX (US); Louis R. Brown, La Jolla, CA (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 141 days.

(21) Appl. No.: 16/891,112

(22) Filed: Jun. 3, 2020

(65) Prior Publication Data
US 2021/0047604 A1    Feb. 18, 2021

Related U.S. Application Data

(60) Provisional application No. 62/886,241, filed on Aug. 13, 2019.

(51) Int. Cl.
*C12M 1/00* (2006.01)
*A01G 33/00* (2006.01)
(Continued)

(52) U.S. Cl.
CPC ............ *C12M 41/20* (2013.01); *A01G 33/00* (2013.01); *C11B 3/00* (2013.01); *C12M 29/00* (2013.01);
(Continued)

(58) Field of Classification Search
CPC ...... C12M 41/20; C12M 33/12; C12M 47/06; C12M 33/10; C12M 47/20; C12M 47/02;
(Continued)

(56) References Cited

U.S. PATENT DOCUMENTS

| 2011/0092726 A1* | 4/2011 | Clarke | ...................... C01C 1/04 554/175 |
| 2015/0143806 A1* | 5/2015 | Friesth | ...................... F03G 7/04 60/517 |

(Continued)

FOREIGN PATENT DOCUMENTS

| CN | 106745769 A | * | 5/2017 | ............... F24T 10/10 |
| WO | WO-2008130974 A2 | * | 10/2008 | ............... C11C 1/10 |
| WO | WO-2012151447 A2 | * | 11/2012 | ............... F24T 10/10 |

OTHER PUBLICATIONS

CN-106745769-A English Machine Translation (provided by Espacenet on Sep. 9, 2021) (Year: 2017).*

*Primary Examiner* — Lydia Edwards
(74) *Attorney, Agent, or Firm* — Shook, Hardy & Bacon L.L.P.

(57) ABSTRACT

A system includes an algae bioreactor that contains an algae slurry, a heat exchanger in fluid communication with the algae bioreactor to receive the algae slurry from the algae bioreactor and heat and increase a pressure of the algae slurry, and one or more valves and a flash vessel in fluid communication with a discharge of the heat exchanger to flash the algae slurry and create steam and algae biomass. A separator receives the algae biomass from the flash vessel and separates oils from the algae biomass to generate a biofuel.

11 Claims, 2 Drawing Sheets

(51) Int. Cl.
- *C11B 3/00* (2006.01)
- *C12M 1/02* (2006.01)
- *C12M 1/26* (2006.01)
- *C12M 1/42* (2006.01)
- *C12N 1/06* (2006.01)
- *F24S 23/71* (2018.01)
- *F24S 70/00* (2018.01)
- *F24S 90/00* (2018.01)
- *F24S 80/00* (2018.01)

(52) U.S. Cl.
CPC ............ *C12M 31/04* (2013.01); *C12M 33/10* (2013.01); *C12M 33/12* (2013.01); *C12M 35/04* (2013.01); *C12M 43/08* (2013.01); *C12M 47/02* (2013.01); *C12M 47/06* (2013.01); *C12M 47/10* (2013.01); *C12M 47/20* (2013.01); *C12N 1/06* (2013.01); *F24S 23/71* (2018.05); *F24S 70/00* (2018.05); *F24S 90/00* (2018.05); *F24S 2080/017* (2018.05)

(58) Field of Classification Search
CPC ...... C12M 47/10; C12M 29/00; C12M 35/04; C12M 31/04; C12M 43/08; C12M 21/02; C11B 3/00; C11B 1/06; C11B 1/04; A01G 33/00; F24S 23/71; F24S 70/00; F24S 90/00; F24S 2080/017; F24S 10/95; F24S 80/50; C12N 1/06; Y02P 60/87; C11C 3/003; C11C 3/12; A23K 10/37; Y02E 10/40; Y02A 40/08; Y02A 40/80

See application file for complete search history.

(56) References Cited

U.S. PATENT DOCUMENTS

2016/0045841 A1* 2/2016 Kaplan .................. B01D 53/48
                429/49
2018/0258384 A1* 9/2018 Dayrell .................. C12M 23/42

* cited by examiner

SOLAR STEAM EXPLOSION OF ALGAE

CROSS-REFERENCE TO RELATED APPLICATIONS

This application claims the benefit of U.S. Provisional Application No. 62/886,241 filed Aug. 13, 2019, which is herein incorporated by reference in its entirety.

BACKGROUND OF THE INVENTION

Concerns about climate change, carbon dioxide ($CO_2$) emissions, and depleting mineral oil and gas resources have led to widespread interest in the production of biofuels from algae, including microalgae. As compared to other plant-based feedstocks, algae have higher $CO_2$ fixation efficiencies and growth rates, and growing algae can efficiently utilize wastewater, biomass residue, and industrial gases as nutrient sources.

Algae are photoautotrophic organisms, or organisms that can survive, grow, and reproduce with energy derived entirely from the sun through the process of photosynthesis. Photosynthesis is essentially a carbon recycling process through which inorganic $CO_2$ combines with solar energy, other nutrients, and cellular biochemical processes to output gaseous oxygen and to synthesize carbohydrates and other compounds critical to the life of the algae.

Algae biomass is generally grown in a water slurry contained within a growth system, which can include both open and closed bioreactor systems. Since they utilize a light source to cultivate photoautotrophic organisms, algae bioreactors are sometimes referred to as "photobioreactors" (PBRs). The most common types of bioreactors used in algal cultivation are open raceway ponds and tubular-type enclosed or open reactors. Various processing methods separate the algal biomass from the water and extract lipids (oils) for the production of fuel and other oil-based products. The remaining wastewater and biomass residue can be recycled or otherwise used in a variety of sustainable applications. For example, the wastewater can form some or all of a subsequent water slurry and the biomass residue can be used as animal feed.

One traditional process of extracting lipids (oil) from algae includes processing the algae slurry to obtain about 1 gram of algae per liter of water. This is then turned into a paste comprising between about 15-20 wt % algae, which is then dried to a moisture level of 10% or less. The dried material is then processed in an extruder or another type of mechanical shearing device that lyses (tears) the algae cell walls and exposes the internal organelles that include the lipids. Various chemicals (e.g., hexane) may then be used to extract the lipids for biofuel production. As will be appreciated, this process requires an enormous amount of energy to get the algae biomass to 10% moisture content.

SUMMARY OF THE INVENTION

The present disclosure is related to biofuel production from algae and, more particularly, to systems and methods of heating an algae slurry and flashing the slurry across one or more valves to lyse the algae cells in preparation for biofuel processing.

In some embodiments, a system is disclosed and includes an algae bioreactor that contains an algae slurry, a heat exchanger in fluid communication with the algae bioreactor to receive the algae slurry from the algae bioreactor and heat and increase a pressure of the algae slurry, and one or more valves and a flash vessel in fluid communication with a discharge of the heat exchanger to flash the algae slurry and create steam and algae biomass. A separator may receive the algae biomass from the flash vessel and separate oils from the algae biomass to generate a biofuel.

In one or more embodiments, a method is disclosed and includes the steps of conveying an algae slurry to a heat exchanger, heating and increasing a pressure of the algae slurry in the heat exchanger, and flashing the algae slurry across one or more valves and depositing the algae slurry in a flash vessel to thereby create steam and algae biomass. The algae biomass may then be processed to generate a biofuel.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to biofuel production from algae and, more particularly, to systems and methods of heating an algae slurry and flashing the slurry across one or more valves to lyse the algae cells in preparation for biofuel processing.

Lipid extraction from algae for biofuel processing is currently practiced by drying algae to 10% or less moisture before running the biomass through a shearing device (e.g., a steam expander or extruder with steam addition) to lyse the cells, at which point the biomass can undergo liquid-liquid extraction. Embodiments disclosed herein describe methods and systems for conducting wet lysing of algae cells from a solution that is 90+% moisture, thus providing significant savings. One method includes conveying an algae slurry to a heat exchanger, heating and increasing a pressure of the algae slurry in the heat exchanger, and flashing the algae slurry across one or more valves and depositing the algae slurry in a flash vessel to thereby create steam and algae biomass. The algae biomass may then be processed to generate a biofuel.

Figure 1:
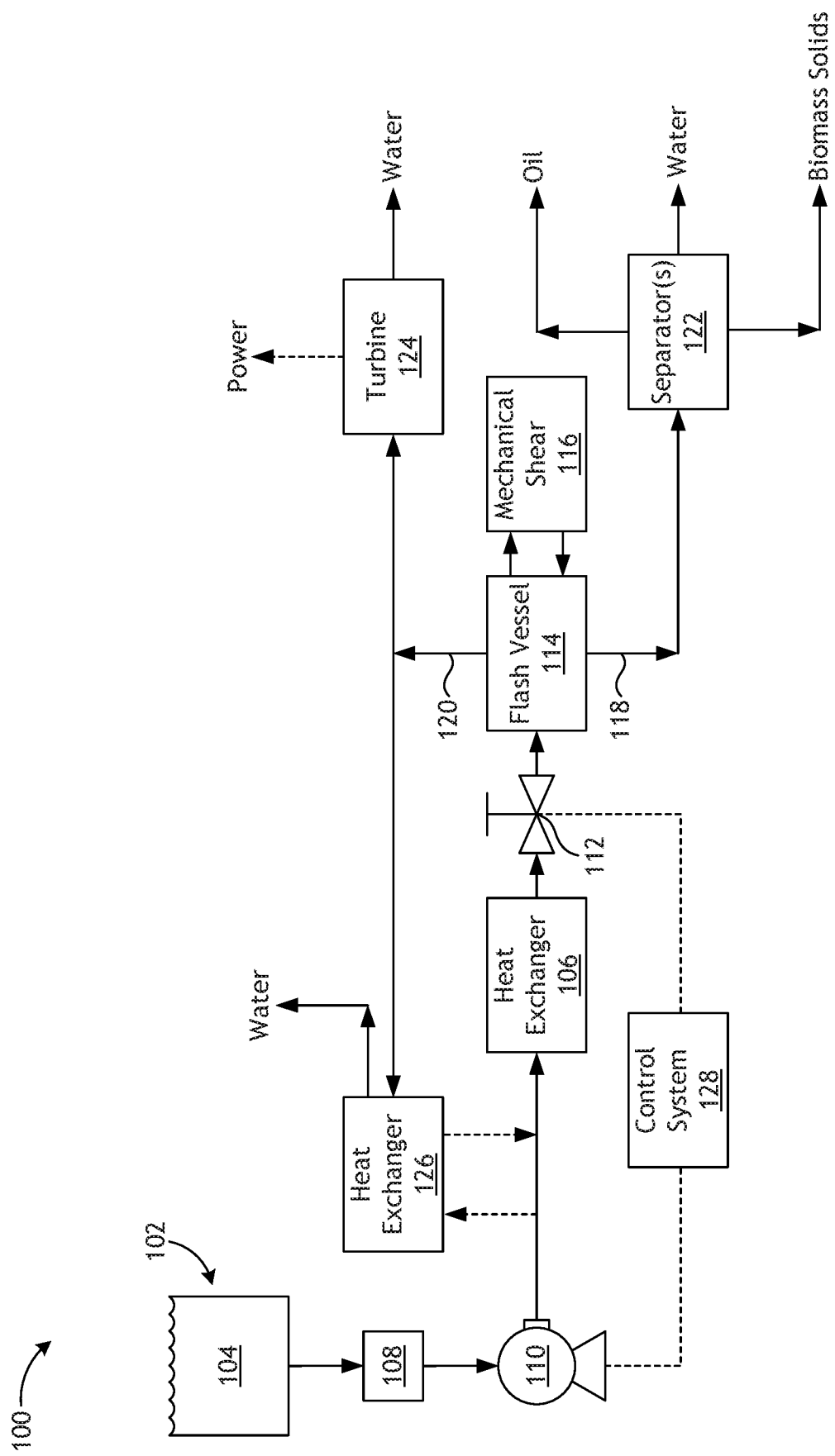
FIG. 1 is a schematic diagram of an example system for processing algae for biofuel production, according to one or more embodiments.

FIG. 1 is a schematic diagram of an example system 100 for processing algae to be used in biofuel production, according to one or more embodiments. As illustrated, the system 100 may include an algae bioreactor 102 (or photobioreactor) configured to contain an aqueous culture of photosynthetic microorganisms, referred to herein as an algae slurry 104. The algae slurry 104 may generally comprise water combined with an algae culture seed stock, maintained in conditions suitable for the growth and harvesting of algae for biofuel production.

Algal sources for preparing the algae culture seed stock for the algae slurry 104 include, but are not limited to, unicellular and multicellular algae. Examples of such algae can include, but are not limited to, a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

The bioreactor 102 may comprise any type of reactor suitable for the growth and harvesting of photosynthetic algae strains. The bioreactor 102 may comprise, for example, an open raceway pond or a tubular-type enclosed or open reactor, as generally known in the art.

The algae slurry 104 harvested and extracted from the bioreactor 102 may comprise 1-20 wt % algae (at least 10 wt % preferred) before being introduced into a heat exchanger 106. In some embodiments, to achieve a concentration of 1-20 wt % algae, the algae slurry 104 may pass through or may otherwise be processed in a separator 108 configured to increase the concentration of the algae within the algae slurry 104. The separator 108 may comprise, for example, a membrane separator or a centrifuge.

In some embodiments, the system 100 may include a pump 110 configured to help convey the algae slurry 104 to the heat exchanger 106. Alternatively, the pump 110 may be omitted and hydrostatic pressure within the bioreactor 102 may be sufficient to convey the algae slurry 104 to the heat exchanger 106.

The heat exchanger 106 may comprise any type of heat exchanging device, apparatus, or system capable of increasing the temperature of the incoming algae slurry 104. In some embodiments, the heat exchanger 106 may be powered, such as an electric or fired heat exchanger. In other embodiments, however, the heat exchanger 106 may employ renewable energy resources to heat the algae slurry 104. For example, the heat exchanger 106 may comprise a solar heater, such as a parabolic mirror heater or a solar tower, each of which incorporates mirrors to concentrate the rays of the sun to maximize heat. In other embodiments, the heat exchanger 106 may comprise a geothermal heat exchanger, without departing from the scope of the disclosure.

The heat exchanger 106 may be configured to increase the temperature of the algae slurry 104 to between about 175° C. and 200° C., and preferably between 100° C. and 120° C. Moreover, the pump 110 and the heat exchanger 106 (or the heat exchanger 106 alone) may cooperatively increase the pressure of the algae slurry 104 within the heat exchanger 106. For example, in some embodiments, the pressure of the algae slurry 104 can be increased to a pressure ranging between about 75 pounds per square inch gauge (psig) and about 600 psig. In other embodiments, however, the pressure of the algae slurry 104 may be increased to as high as 1000 psig, without departing from the scope of the disclosure.

The high-pressure, high-temperature algae slurry 104 discharged from the heat exchanger 106 may then be flashed (let down) across one or more valves 112 and deposited in a flash vessel 114. Flashing the algae slurry 104 across the valve(s) 112 will decrease the pressure of the algae slurry 104 and simultaneously cause a rapid expansion of vapor, commonly referred to as "steam explosion." This creates a high shear environment within the flash vessel 114 that lyses (e.g., tears, rips apart, etc.) the algae cells to provide access to the internal organelles and lipids (oils). In some embodiments, an acid may be added to the flash vessel 114 to assist in lysing the algae cells. Acids can react with the cell wall, weaken it, and start to break it down. Example acids that may be used include, but are not limited to, sulfuric, phosphoric, nitric, hydrochloric, or any combination thereof.

While one valve 112 is depicted in the system 100, it is contemplated herein to employ a plurality of valves 112 and flash the high-pressure, high-temperature algae slurry 104 across multiple valves 112. In such embodiments, a first valve 112 may be configured to decrease the pressure of the algae slurry 104 from around 600 psig to around 300 psig, and a second valve 112 may be configured to decrease the pressure of the algae slurry 104 from around 300 psig to ambient. Alternatively, the second valve 112 may be configured to decrease the pressure of the algae slurry 104 from around 300 psig to about 15 psig, and a fourth valve 112 may be configured to decrease the pressure of the algae slurry 104 from around 15 psig to ambient. As will be appreciated, additional valves may be employed and designed to flash the algae slurry 104 to differing pressure thresholds, without departing from the scope of the disclosure. Moreover, flashing the algae slurry 104 across multiple valves 112 provides multiple opportunities to shear the algae cell with only one pressurization (pumping) stage. In some applications, for instance, a first flashing stage may rupture the cell wall, while subsequent flashing stages may rupture the internal organelles containing lipids. This may also add robustness of operation as cells vary in their properties.

The flash vessel 114 may be a type of vapor/liquid separator that receives the flashed algae slurry 104 and results in the creation of steam separated from algae biomass consisting of a mixture of liquids, solids, and oils. In some embodiments, the flash vessel 114 may include or may otherwise be fluidly coupled to a mechanical shearing device 116 configured to assist in lysing the algae cells as needed to access the lipids (oils). The mechanical shearing device 116 may include, but is not limited to, a blender, a rotor/stator combination, a high shear pump, a homogenizer, or any combination thereof.

The algae biomass (i.e., mixture of liquids, solids, and oils), alternately referred to as the "bottoms," congregates near the bottom of the flash vessel 114 and is separated from the vapors and gases (e.g., steam), which congregate near the top of the flash vessel 114. The algae biomass may be discharged from the flash vessel 114 via a bottoms conduit 118, and the steam may be discharged from the flash vessel 114 via a steam conduit 120.

The algae biomass discharged from the flash vessel 114 may be conveyed to a separator 122 to separate the algae biomass into phases of oil, water, and biomass solids (e.g., leftover algae bodies). In some embodiments, the separator 122 may comprise a density and gravity separator, such as an American Petroleum Institute (API) oil-water separator. In other embodiments, the separator 122 may comprise a three-phase decanter centrifuge operable to separate the algae biomass into oil, water, and biomass solids phases. In yet other embodiments, the separator 122 may comprise a combination of the API separator and the three-phase decanter centrifuge, without departing from the scope of the disclosure. The three-phase decanter centrifuge may be preferred since it may not generate a rag layer, which may occur with the API separator.

The oil phase generated in the separator 122 may include fatty organelles that contain fats and lipids that float to the top and can be extracted (e.g., skimmed) for biofuel production, such as biodiesel, or may be hydrotreated to generate renewable diesel that contains no oxygen heteroatoms. Processing the oil into a biofuel may further include process steps such as refining, bleaching, deodorizing, etc. The water phase may include surfactants that prevent the water from meeting discharge (disposal) requirements. In such cases, the water may be conveyed to a wastewater treatment facility for proper treatment and/or disposal. The biomass solids includes leftover parts of the algae, including proteins, carbohydrates, membranes, DNA, etc. These materials may be disposed of or alternately used in animal feeds.

The steam generated in the system 100 may be used for various useful purposes. In some embodiments, for example, the steam conduit 120 may convey the steam to a turbine 124 to generate electric power. In such embodiments, the turbine 124 may comprise a condensing turbine or a backpressure turbine. The warm water derived from the condensed steam may largely comprise fresh water substantially reduced in salinity and usable for a variety of purposes. In some embodiments, for example, the water may be used as a source of potable water. In other embodiments, the water can be used as a source of make-up water for the bioreactor 102. In yet other embodiments, the water can be used to wash salt from the biomass solids discharged from the separator(s) 122 and thereby reduce the salinity concentration of the biomass solids. The water generated by the turbine 124 may be employed in any combination of the foregoing applications, without departing from the scope of the disclosure.

In other embodiments, or in addition thereto, the steam conduit 120 may convey the steam to a heat exchanger 126 configured to interact with and pre-heat the algae slurry 104 prior to entering the heat exchanger 106. The heat exchanger 126 may include, but is not limited to, a shell and tube heat exchanger, a plate heat exchanger, a plate and shell heat exchanger, an adiabatic wheel heat exchanger, a plate fin heat exchanger, a pillow plate heat exchanger, a fluid heat exchanger, a helical-coil heat exchanger, a spiral heat exchanger, or any combination thereof. As will be appreciated, heating the algae slurry 104 prior to entering the heat exchanger 106 may reduce the load requirement on the heat exchanger 106, thus making the process and system 100 more efficient. Moreover, the water generated by condensing the steam in the heat exchanger 126 may be used for any of the applications mentioned above for the water derived from the turbine 124.

The system 100 may further include a control system 128 configured or otherwise programmed to operate the system 100. In some embodiments, the control system 128 may be communicably coupled (wired or wireless) to the pump 110 to regulate the residence time of the algae slurry 104 through the heat exchanger 106. The control system 128 may also be communicably coupled to the valve(s) 112 to control operation of the valve(s) 112. In order to achieve proper lysing of the algae cells, the residence time of the algae solution 104 within the heat exchanger 106 and the flashing velocity across the valve(s) 112 may have to be varied, preferably by volumetric flow rate changes.

Figure 2:
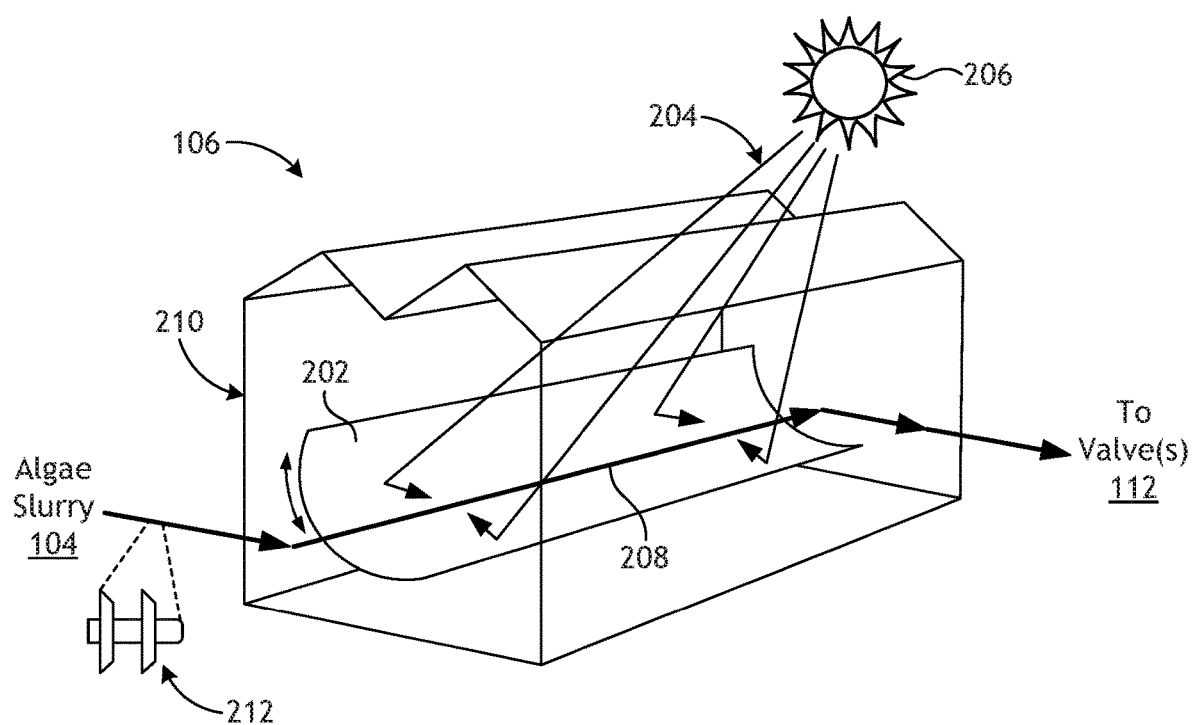
FIG. 2 is a schematic diagram of an example of the heat exchanger of FIG. 1, according to one or more embodiments.

FIG. 2 is a schematic diagram of an example of the heat exchanger 106, according to one or more embodiments. In the illustrated embodiment, the heat exchanger 106 may comprise a solar heater that includes a parabolic mirror 202 configured and otherwise situated to reflect and redirect rays 204 emanating from the sun 206 toward a heat pipe 208. As the algae slurry 104 is conveyed through the heat pipe 208, the parabolic mirror 202 concentrates (focuses) the reflected rays 204 onto the heat pipe 208 and thereby increases the temperature of the pipe 208 and, consequently, the algae slurry 104 circulating therethrough. While the heat pipe 208 is depicted as a straight section of pipe, it is contemplated herein that the heat pipe 208 include multiple interconnected turns and straight sections that allow the algae slurry 104 to traverse a tortuous pathway as it heats.

In some embodiments, as illustrated, at least a portion of the solar heater may be positioned within a greenhouse 210 having transparent walls. Arranging the parabolic mirror 202 within the greenhouse 210 may prove advantageous in eliminating the need to brace the parabolic mirror 202 against high winds that may inadvertently unfocus the mirror 202 off the heat pipe 208. Moreover, the greenhouse 210 may prevent ash (e.g., debris, dirt, dust, etc.) from congregating on the mirror 202 and thereby diminishing its reflective potential.

As the sun 206 rises and sets, the reduced solar irradiance will not provide as large of a heat flux as at mid-day. Accordingly, the control system 128 (FIG. 1) may be configured or programmed to operate the pump 110 (FIG. 1) and the valve(s) 112 (FIG. 1) to regulate the residence time of the algae slurry 104 through the heat pipe 208. For example, the control system 128 may operate the pump 110 and/or the valve(s) 112 such that the volumetric throughput of the algae slurry 104 through the heat pipe 208 will be slower during low solar times (e.g., cloudy, early or late hours of day, etc.), and higher during high solar times (e.g., clear skies, middle of day, etc.). Alternatively, or in addition thereto, flow rate can be decreased while reducing the number of passes through a fixed length of the heat pipe 208. This approach has the advantage of controlling surface temperature of the heat pipe 208 with flow rate (e.g., convective heat removal) while keeping residence time of the algae slurry 104 similar throughout the day.

In some embodiments, the heat exchanger 106 may include or otherwise incorporate a pigging system configured to remove fouling and debris on the inner walls of the heat pipe 208. More specifically, an inline pig 212 may be introduced into the heat pipe 208 and pumped through the heat pipe 208 to clear it of fouling and debris.

Embodiments Listing

The present disclosure provides, among others, the following embodiments, each of which may be considered as optionally including any alternate embodiments.

Clause 1. A system that includes an algae bioreactor that contains an algae slurry, a heat exchanger in fluid communication with the algae bioreactor to receive the algae slurry from the algae bioreactor and heat and increase a pressure of the algae slurry, one or more valves and a flash vessel in fluid communication with a discharge of the heat exchanger to flash the algae slurry and create steam and algae biomass, and a separator that receives the algae biomass from the flash vessel and separates oils from the algae biomass to generate a biofuel.

Clause 2. The system of Clause 1, wherein the algae slurry comprises a concentration of 1-20 wt % algae.

Clause 3. The system of Clause 2, further comprising a separator that fluidly interposes the algae bioreactor and the heat exchanger, the separator being operable to receive the algae slurry and increase the concentration of the algae to 1-10 wt %.

Clause 4. The system of any of Clauses 1 to 3, further comprising a pump that conveys the algae slurry to the heat exchanger.

Clause 5. The system of Clause 4, further comprising a control system in communication with at least one of the one or more valves and the pump to regulate a residence time of the algae slurry within the heat exchanger.

Clause 6. The system of any of Clauses 1 to 5, further comprising a mechanical shearing device fluidly coupled to the flash vessel and operable to assist in lysing algae cells of the algae slurry.

Clause 7. The system of any of Clauses 1 to 6, wherein the separator comprises at least one of an API oil-water separator and a three-phase decanter centrifuge.

Clause 8. The system of any of Clauses 1 to 7, further comprising a turbine fluidly coupled to the flash vessel to receive steam from the flash vessel and generate electrical power.

Clause 9. The system of any of Clauses 1 to 8, wherein the heat exchanger is a first heat exchanger and the system further comprises a second heat exchanger fluidly coupled to the flash vessel to receive steam from the flash vessel and preheat the algae slurry within the second heat exchanger prior to being introduced into the first heat exchanger.

Clause 10. The system of any of Clauses 1 to 9, wherein the heat exchanger is selected from the group consisting of an electric heat exchanger, a fired heat exchanger, a solar heater, a geothermal heat exchanger, and any combination thereof.

Clause 11. The system of any of Clauses 1 to 10, wherein the heat exchanger is a solar heater comprising a heat pipe that receives the algae slurry, and a parabolic mirror situated to reflect and redirect rays emanating from the sun toward a heat pipe to heat the algae slurry.

Clause 12. The system of Clause 11, wherein at least a portion of the solar heater is arranged within a greenhouse.

Clause 13. The system of Clause 11, further comprising an inline pig conveyable along the heat pipe to clear the heat pipe of fouling and debris.

Clause 14. A method includes conveying an algae slurry to a heat exchanger, heating and increasing a pressure of the algae slurry in the heat exchanger, flashing the algae slurry across one or more valves and depositing the algae slurry in a flash vessel to thereby create steam and algae biomass, and processing the algae biomass to generate a biofuel.

Clause 15. The method of Clause 14, wherein conveying the algae slurry to the heat exchanger comprises conveying the algae slurry with a concentration of 1-10 wt % algae.

Clause 16. The method of Clause 14 or 15, wherein conveying the algae slurry to the heat exchanger comprises pumping the algae slurry into the heat exchanger with a pump.

Clause 17. The method of Clause 16, wherein the heat exchanger comprises a solar heater that includes a mirror and a heat pipe, the method further comprising circulating the algae slurry through the heat pipe, and concentrating sunlight on the heat pipe with the mirror and thereby heating the heat pipe and the algae slurry.

Clause 18. The method of Clause 16, further comprising controlling operation of at least one of the one or more valves and the pump with a control system and thereby regulating a residence time of the algae slurry within the heat exchanger.

Clause 19. The method of any of Clauses 14 to 18, wherein flashing the algae slurry across the one or more valves comprises creating a high shear environment that that lyses algae cells of the algae media and generates the algae biomass.

Clause 20. The method of Clause 19, further comprising adding an acid to the flash vessel to assist in lysing the algae cells.

Clause 21. The method of Clause 19, further comprising conveying the algae slurry to a mechanical shearing device fluidly coupled to the flash vessel, and operating the mechanical shearing device to assist in lysing the algae cells.

Clause 22. The method of any of Clauses 14 to 21, wherein the one or more valves comprise a plurality of valves and flashing the algae slurry across the one or more valves comprises flashing the algae slurry across a first valve to reduce the pressure of the of the algae slurry from a first pressure to a second pressure less than the first pressure, and flashing the algae slurry across a second valve to reduce the pressure of the of the algae slurry from the second pressure to a third pressure less than the second pressure.

Clause 23. The method of any of Clauses 14 to 22, wherein processing the algae biomass to generate the biofuel comprises extracting the algae biomass from the flash vessel; separating oil from the algae biomass in one or more separators, and refining the oil to generate the biofuel.

Clause 24. The method of any of Clauses 14 to 23, further comprising conveying the steam to a turbine, and generating electrical power with the turbine and the steam.

Clause 25. The method of any of Clauses 14 to 24, wherein the heat exchanger is a first heat exchanger, the method further comprising conveying the steam to a second heat exchanger, and heating the algae slurry in the second heat exchanger prior to entering the first heat exchanger.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A system, comprising:
   an algae bioreactor configured to contain an algae slurry;
   a heat exchanger in fluid communication with the algae bioreactor and comprising a solar heater including a heat pipe configured to contain the algae slurry and a parabolic mirror situated to reflect and redirect rays emanating from the sun toward the heat pipe to heat and pressurize the algae slurry within the heat pipe, wherein the heat pipe is constructed to maintain an internal pressure of at least about 75 pounds per square inch gauge (psig);
   one or more valves arranged at a discharge of the heat exchanger and sized to cause a pressure drop of at least 50 psig on fluid entering the one or more valves at a pressure of at least about 75 psig, wherein a 50 psig pressure drop generates a high shear environment that lyses algae cells of the algae slurry to generate an algae biomass;
   a control system in communication with the one or more valves and operable to regulate a residence time of the algae slurry within the heat pipe based on solar irradiance;
   a flash vessel in fluid communication with an outlet side of the one or more valves; and
   a separator that receives the algae biomass from the flash vessel and separates oils from the algae biomass to generate a biofuel.

2. The system of claim 1, wherein the algae slurry comprises a concentration of 1-20 wt % algae.

3. The system of claim 2, wherein the separator is a first separator and the system further comprises a second separator that fluidly interposes the algae bioreactor and the heat exchanger, the second separator being operable to receive the algae slurry and increase the concentration of the algae to 1-10 wt %.

4. The system of claim 1, further comprising a pump that conveys the algae slurry to the heat exchanger.

5. The system of claim 4, wherein the control system is further in communication with the pump to help regulate the residence time of the algae slurry within the heat pipe.

6. The system of claim 1, further comprising a mechanical shearing device fluidly coupled to the flash vessel and operable to assist in lysing algae cells of the algae slurry.

7. The system of claim 1, wherein the separator comprises at least one of an API oil-water separator and a three-phase decanter centrifuge.

8. The system of claim 1, further comprising a turbine fluidly coupled to the flash vessel to receive steam from the flash vessel and generate electrical power.

9. The system of claim 1, wherein the heat exchanger is a first heat exchanger and the system further comprises a second heat exchanger fluidly coupled to the flash vessel to receive steam from the flash vessel and preheat the algae slurry within the second heat exchanger prior to being introduced into the first heat exchanger.

10. The system of claim 1, further comprising a greenhouse, wherein the heat pipe extends through the greenhouse, and the parabolic mirror is arranged within the greenhouse.

11. The system of claim 1, further comprising an inline pig conveyable along the heat pipe to clear the heat pipe of fouling and debris.

* * * * *